(12) United States Patent
Luther et al.

(10) Patent No.: US 7,871,164 B2
(45) Date of Patent: Jan. 18, 2011

(54) OPHTHALMOLOGICAL INSTRUMENT

(75) Inventors: Egon Luther, Jena-Cospeda (DE); Ingo Koschmieder, Jena (DE); Manfred Dick, Gefell (DE); Joachim Winter, Jena (DE); Uwe Mohrholz, Jena (DE); Thomas Mohr, Jena (DE); Daniel Bublitz, Jena (DE); Enrico Geissler, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 38 days.

(21) Appl. No.: 12/281,134

(22) PCT Filed: Feb. 22, 2007

(86) PCT No.: PCT/EP2007/001527

§ 371 (c)(1),
(2), (4) Date: Aug. 28, 2008

(87) PCT Pub. No.: WO2007/098882

PCT Pub. Date: Sep. 7, 2007

(65) Prior Publication Data

US 2009/0257024 A1     Oct. 15, 2009

(30) Foreign Application Priority Data

Feb. 28, 2006     (DE) .................... 10 2006 010 105

(51) Int. Cl.
*A61B 3/10* (2006.01)
*A61B 3/14* (2006.01)

(52) U.S. Cl. ...................... 351/205; 351/206
(58) Field of Classification Search .......... 351/200–246
See application file for complete search history.

(56) References Cited

U.S. PATENT DOCUMENTS

| 4,699,482 A | 10/1987 | Utsugi .................. 351/206 |
| 5,997,141 A | 12/1999 | Heacock ................ 351/221 |
| 6,142,629 A * | 11/2000 | Adel et al. ............. 351/206 |
| 2008/0019127 A1 * | 1/2008 | Dick et al. ............. 362/235 |

FOREIGN PATENT DOCUMENTS

| DE | 10 2004 020 663 A1 | 11/2005 |
| DE | 10 2005 020 695 A1 | 12/2005 |
| EP | 1 114 608 A1 | 7/2001 |
| EP | 1 602 323 A1 | 12/2005 |
| WO | WO 2006/016366 A2 | 2/2006 |

* cited by examiner

*Primary Examiner*—Mohammed Hasan
(74) *Attorney, Agent, or Firm*—Patterson Thuente Christensen Pedersen, P.A.

(57) ABSTRACT

A homogeneously illuminating ophthalmic instrument includes an illumination device having a source of illumination, a homogenizing unit and a projection device, at least one organic or inorganic source of radiation with spectrally selective emission being used as a source of illumination. The illumination generated in this way enables correspondingly adapted visual and/or digital observation, recording or display of the examined regions of the eye by a visualizing unit.

32 Claims, 1 Drawing Sheet

OPHTHALMOLOGICAL INSTRUMENT

The present application is a National Phase entry of PCT Application No. PCT/EP2007/001527, filed Feb. 22, 2007, which claims priority from German Application Number 10 2006 010 105.7, filed Feb. 28, 2006, the disclosures of which are hereby incorporated by reference herein in their entirety.

FIELD OF THE INVENTION

The present invention relates to an instrument for observation, documentation and/or diagnosis of an eye, in particular of the anterior portion of the eye, the iris, the lens, the vitreous body, as well as the fundus of the eye.

BACKGROUND OF THE INVENTION

According to the known prior art, classic ophthalmic instruments for examination of the eye use conventional white light sources for illumination, so as to generate an image of the eye's interior that is as natural as possible for the observer. In order to enable examinations in specific spectral ranges, suitable spectral filters are inserted in the beam path following the white light source.

These conventional white light sources, such as e.g. halogen lamps, have the disadvantage that, from an energetic and economic point of view, the light is generated only with a relatively low efficiency of 8-12%. Moreover, a considerable part of the spectrum is located outside the visible range, and the UV and IR components have to be filtered out in order to prevent the illumination damaging the eye.

This disadvantage is even more pronounced where only very narrow spectral ranges, e.g. from the UV range, are used to carry out fluorescence examinations. Accordingly, this conventional illumination requires very complex technical equipment for the mechanically movable optical filters and for cooling the system.

A further disadvantage of conventional white light sources is their switch-on and switch-off behavior, which is characterized, on the one hand, by relatively long switching times (in the range of >100 ms) and, on the other hand, by variation of the spectral composition of the light during the switch-on phase. Moreover, halogen lamps have a relatively long warm-up phase.

In the slit lamps known from the prior art, which use halogen lamps, the light of the halogen lamp is parallelized by a condenser lens and then illuminates a slit whose width is adjustable. The light passing through the slit is then imaged sharply by an optical system into the anterior chamber of the eye to be examined. Light scattered back by the eye is imaged onto a camera by second detection optics and/or enables visual observation of the eye. In order to be able to vary the angle between the illumination and detection beam paths, the illumination beam path is bent in front of the eye by a prism. This deflecting prism is located approximately in the pupil plane in front of the eye. Since all illumination beams have to transmit through the prism exit surface, said deflecting prism limits the étndue of the source of illumination. In this respect, it is important for the light passing through the slit in the source of illumination to be as homogeneous as possible, because said homogeneity is transmitted as far as the focal plane of the slit lamp due to the imaging into the eye.

Since the homogeneous slit illumination is achieved in the prior art by a condenser lens arranged preceding the halogen lamp, the slit is located in the pupil plane of the halogen lamp's spiral-wound filament, so that the homogeneity in the slit plane thus corresponds to the homogeneity of intensity in the angular spectrum of the halogen lamp's spiral-wound filament.

Due to the relatively long switching times, there is a need, particularly in the case of short exposure times, for an additional, quick shutter which puts the light of a "burnt-in" lamp to its actual use. This is disadvantageous, in particular, in the case of moving objects under examination, such as the eye, because very short exposure times in the ms range are needed here in order to exclude influences of motion when documenting the eye.

Document EP 1,114,608 B1 describes a known embodiment of an ophthalmic irradiation system using in a subcomponent of the total system an illumination on the basis of LEDs. It is set forth in the dependent claims that the device substantially serves to emit certain quantities of red, green, and blue light so as to generate substantially white light. The individual light regulation serves to maintain the respective shade when the protective filter is swiveled in or swiveled out, respectively. Thus, in a special alternative embodiment, the document EP 1,114,608 B1 describes an illumination system on the basis of LEDs, which serves to maintain neutrality in color in combination with an optical protective filter.

Document EP 1,602,323 A1 describes the use of a white LED as the source of illumination in a classic slit lamp. In contrast to the already described classic slit lamp illumination, the homogeneity in the slit plane corresponds to the homogeneity of intensity in the angular spectrum of the LED chip surface here. However, since there is a clear difference between the optical properties of the light emission of a spiral-wound filament and an LED chip surface, this also has negative effects on the achievable homogeneity. Due to the curved shape of the incandescent wire, a spiral-wound filament emits an approximately spherical wave with a homogeneous intensity in the angular spectrum. In contrast thereto, an LED chip functioning as a planar emitter emits, with good approximation, a Lambert angular spectrum. This means that the light intensity decreases with the cosine to the LED chip surface normal, causing systematic trimming in the slit plane. Said trimming depends on the aperture of the condenser lens, and an aperture of NA=1 corresponds to 100% trimming. Such trimming cannot be avoided completely in case of a "Koehler" illumination, but can only be reduced by limiting the aperture of the condenser lens, which on the other hand strongly reduces the energy efficiency of the source of illumination, however. A particular advantage of this apparatus—as compared to slit lamps on the basis of halogen lights—is the light's high consistency in color at different intensities. Thus, EP 1,602,323 A1 describes a classic slit lamp using as a source of radiation a white LED or red, green, and blue LEDs, respectively, to generate white light.

Document U.S. Pat. No. 5,997,141 A describes a system which uses arrays of LEDs for illumination of the eye. Document U.S. Pat. No. 4,699,482 A describes an illumination device which uses LEDs in combination with light-conducting fibers for illumination of the eye.

All these documents relating to spatially distributed emitters have the disadvantage—in the absence of special devices for homogenization—that the intensity in the field of illumination is not sufficiently homogeneous and does not suffice for a sensitive diagnosis.

SUMMARY OF THE INVENTION

It is an object of the present invention to provide a solution for an energetically economic illumination device of improved applicability for an ophthalmic instrument, said device being characterized, in particular, by spectrally selective, very homogeneous generation of light with multiple-channel capability, short switching times and high spectral stability in switch-on emission and short-time emission.

A particularly advantageous applicative property of this novel illumination device is, for example, the possibility of providing high spectrally selective intensities in the near-UV range of >400 nm, where the ocular media have the greatest scattering power in the visible range, allowing extremely sensitive diagnoses.

On the other hand, the use of LEDs at 1065 or 1300 nm in the region of the lowest scattering of ocular media and even lower water absorption allows examination, e.g. through cataract lenses, the posterior surface and the posterior capsule membrane thereof.

Thus, the concept of the invention describes the use of quite specific spectra in combination with very short switch-on and switch-off times, respectively, with high consistency in color, for the purpose of increasing the sensitivity of diagnosis of the eye.

The invention will be described in more detail below with reference to exemplary embodiments. In this connection,

DETAILED DESCRIPTION

Figure 2:
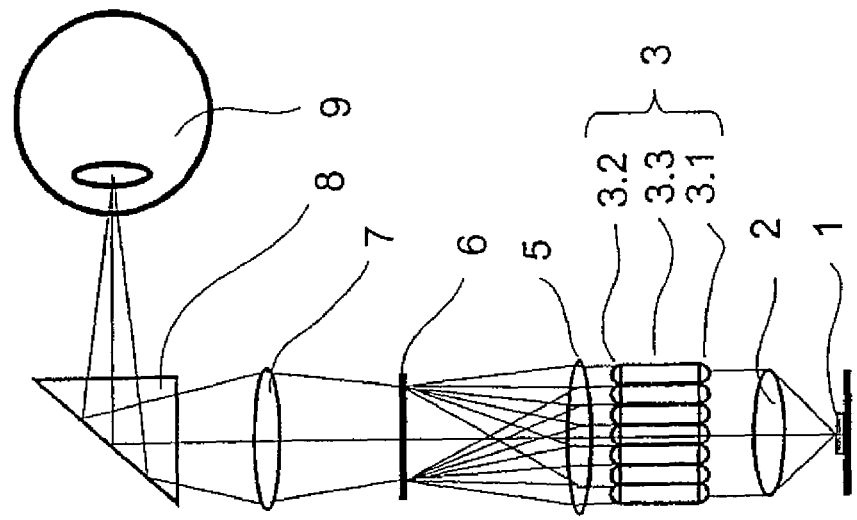
FIG. 2 shows an arrangement for homogenization of light from the sources of radiation on the basis of a hollow integrator.

In the ophthalmic instrument according to the invention—which instrument has homogeneous illumination for observation and/or documentation of an eye and consists of an illumination device including a source of illumination, a homogenizing unit, and a projection device—one or more organic or inorganic sources of radiation with spectrally selective emission are used.

Controlled by a control unit, these sources of radiation generate continuous and/or pulsed spatial illumination in order to enable, via a digital camera unit, suitably adapted visual and/or digital observation, recording, or output of the examined areas of the eye.

In this case, in particular, LEDs, SLDs, lasers or O-LEDs are used individually or in combination as organic or inorganic sources of radiation with spectrally selective emission. The source of illumination preferably comprises several sources of radiation emitting in a spectrally selective manner, which have the same and/or different intensity distributions as a function of their wavelengths. The intensity distributions of the sources of radiation are broad-band, narrow-band or monochromatic distributions or are formed by combinations thereof, respectively.

Whereas sources of radiation in the visible spectral range (white light) have a predominantly broadband intensity distribution, sources of radiation which excite fluorescence have a monochromatic intensity distribution that is as narrowband as possible, having a half width of $\leqq 50$ nm for a preferably Gaussian profile with a central peak.

For emission of a broadband spectrum of for example from 400 to 700 nm, the illumination device comprises one or more sources of radiation which preferably emit a monochromatic (blue) spectrum of from 400 to 490 nm and are coated with a luminescent dye for color conversion. This results in the majority of the emitted white spectrum being located in the blue range. LEDs of the Dragon LW W5SG type from OSRAM are an example of LEDs having such an intensity profile. The color locus is located on the white curve in the chromaticity chart, albeit in the blue range.

Such LEDs, which emit light in the blue range of the white spectrum, have the advantage that higher scattering at the media of the eye occurs in the shorter wavelength range, which enables an improved diagnosis.

In a further embodiment, an LED is used which emits a monochromatic spectrum in the UV range (<400 nm) and is coated with a luminescence dye for color conversion. Such an LED has the advantage that no emission of the excitation wavelength (<400 nm) occurs in the visible range (400-750 nm). In this case, the luminescence dye for color conversion can be provided such that the resulting emission spectrum is approximated to the profile of the V($\lambda$) curve which describes the profile of the spectral sensitivity of the human eye and is thus perceived by the human eye as a nearly "perfect white".

In principle, it is also possible to generate white light from a combination of monochromatic sources of radiation, such as, for example, red, green, and blue LEDs. Here, suitable combinations allow to generate very specific distribution functions of the white light.

For this purpose, LEDs from OSRAM, for example, type LB W5SG (blue), LV W5SG (verde/blue-green), LT W5SG (green), or LE R A2A (red) are used as narrowband, monochromatic LEDs having a half width of $\leqq 50$ nm and a preferably Gaussian distribution with a central peak.

Narrowband illumination enables diagnosis in special spectral ranges. Observation can be effected directly in the visible range or with illumination in the non-visible range by means of an electronic camera and conversion/transmission of information into the visible range, e.g. by means of false color reproduction on a display. For example, colors in a range of from 400-700 nm can be assigned to certain intensity values in the non-visible range and represented on the display.

This has the advantage that desired wavelengths can be selected by actuation of selected monochromatic sources of radiation.

As a result, considerably simplified and improved operation is achieved, because mechanically moved optical filters can be dispensed with.

However, illumination devices for emission of a broadband spectrum are also possible for a spectral range of preferably from 700 to 1100 nm, using one or more sources of radiation with a half width of at least 20 nm.

In this case, a digital camera unit with sensitivity within this spectral range is to be used for visual and/or digital observation, recording, or output.

The (if possible) narrowband, monochromatic intensity distributions of the sources of radiation for excitation of fluorescence range from the UV range to the IR range here. Whereas wavelengths in the UV range from approximately 180 nm are suitable to document the fluorescence images excited by an excimer laser, wavelengths in the IR range up to approximately 2 µm are used to document images with low scattering of the radiation in tissue and still sufficient water absorption. Beginning at a wavelength of greater than 2 µm, the depth of penetration is just about sufficient for the cornea and, thus, no longer suitable for imaging.

For example, LEDs of the OSRAM SFH4230 type, which emit radiation in the range of from 700 to 1100 nm, with a half width of 40 nm and a peak wavelength of 850 nm for a Gaussian distribution, are used as sources of radiation for emission of IR spectra.

Since illumination occurs in the non-visible spectral range here, too, a digital camera unit with sensitivity within this spectral range is required for observation, recording, or output.

This alternative embodiment is particularly advantageous because no, or only a very minor, irritation of the eye occurs which results in narrowing of the pupil and no mydriatic is required. Thus, diagnoses in the IR range are possible by transmission/conversion of information from the IR range into the visible range, e.g. by means of false color reproduction on the display. Reliable diagnoses are possible despite the patient's reduced exposure to radiation.

In a further embodiment, combinations of a broadband source of radiation and monochromatic sources of radiation are also possible in order to generate specific intensity distributions. The combination of sources of radiation, which do not overlap in the spectrum, may preferably be effected by means of dichroic mirrors which are imaged onto one common aperture. Especially when combining different sources of radiation, it is important that the beams generated by the individual sources of radiation are identical in terms of aperture and angle of aperture at the coupling point to the ophthalmic examination instrument.

In another advantageous embodiment, several laser sources are used for illumination. Co-linear imaging of the individual laser beams may preferably be effected by means of an optical grating or a prism. Optionally, the narrowband spectra having a typical half width of, for example, +/−3 nm can be broadened to a half width of +/−20 nm using optical conversion layers. Fluorescence dyes can be used here as optical conversion layers.

In order to generate an intensity distribution which is as uniform as possible, the illumination device comprises a homogenizing unit in the form of a light integrator or light mixer, which is arranged preceding the sources of radiation. In particular, a hollow integrator or a microlens array is used here as a homogenizing unit. Using the homogenizing unit, the light emitted by the sources of radiation is homogenized with respect to its intensity, color and angular spectrum. In doing so, light homogenization is to be effected by adapting the étendues of the sources of radiation to the illumination optics at a maximum possible light efficiency.

Figure 1:
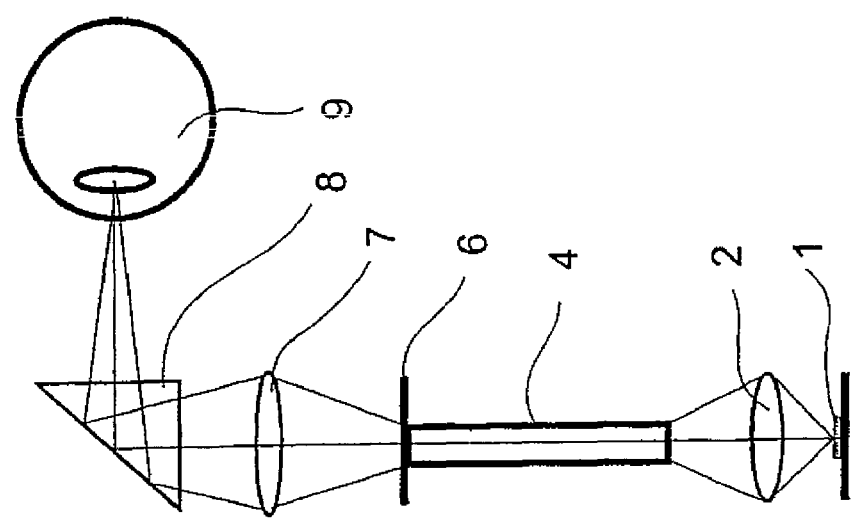
FIG. 1 shows an arrangement for homogenization of light from the sources of radiation on the basis of a microlens array.

In this connection, FIG. 1 shows an arrangement for homogenizing the light of the sources of radiation on the basis of a microlens array. The light coming from the sources of radiation 1 is collimated by a condenser lens 2 and is imaged onto the microlens array 3. The microlens array 3 consists of respectively opposing spherical surfaces 3.1 (input plane) and 3.2 (output plane) with a spacing 3.3 which corresponds to the focal distance of the microlenses. The cooperation of the condenser lens 2 and the microlens array 3 causes the source of radiation 1, which consists e.g. of individual LEDs, to be imaged into the imaging lens 5 in a space-filling manner, if possible, said imaging lens 5 being arranged behind the microlens array 3.

Behind this imaging lens 5, there may be arranged, for example in the image plane 6, a slit diaphragm by which the slit illumination required for a slit lamp is generated. The slit thus generated is projected into the eye 9 via the projecting unit 7 and a deflecting prism 8, with the irradiation angle of the illumination being variable.

The thus-achieved homogenization of the illumination radiation can be made clear as follows:

The pupil of the sources of radiation 1 is located exactly in the input plane 3.1 of the microlens array 3, and the light being distributed by the microlenses into as many channels as there are microlenses present. The light of each channel is then imaged via the imaging lens 5 into the image plane 6, where it has the light of all other channels superimposed upon it. When LEDs having a Lambert radiation profile are used as the source of radiation 1, a cosine-shaped intensity distribution can be observed in the input plane 3.1 of the microlens array 3. However, since the light of each microlens is imaged onto the entire image field through the associated second microlens and the imaging lens 5, near-perfect homogenization can be achieved in the image plane 6. Even the angular spectrum behind the image plane 6 is considerably more homogeneous than in the case of conventional illumination.

An advantageous embodiment provides the use of microlens arrays whose individual lenses have honeycomb-shaped cross-sections. This is advantageous, in particular, for generating a slit illumination. The use of one or more white LEDs has the advantage that the illumination of the slit in the image plane and in the anterior chamber of the eye is substantially more homogeneous than in classic "Koehler" illuminations and has nearly no trimming anymore, which is beneficial especially for realizing high quantity measurements.

In this context, measurement of the opacity of the eye lens caused by grey cataract may be mentioned. This also enables, for example, the use of the brightness of a fluorescent contrast agent as a measure for the size of the gap between the eye and the contact lens when adapting contact lenses.

Even considerably greater improvements in illumination can be achieved by the use of LED arrays having an RGB structure. In LED arrays of this type, the three primary colors (red, green, and blue) are arranged, for example, in a square structure, with the color green being present twice, diagonally opposite each other. If such an LED array is imaged into the eye by classic optics, cut-off errors in the deflecting prism may lead to color distortions and, thus, may cause white slit-shaped illumination to be generated only in the focal plane of the slit image. However, since in a slit lamp sectional images of the eye's anterior chamber are to be recorded simultaneously at different depths, there must be no color artefacts in front of and behind the focal plane. Such color artifacts are prevented by the presently described homogenization using a microlens array.

For these reasons, the use of a homogenizing unit for slit lamp illumination is an important advantage and an essential improvement which goes beyond the prior art concerning the use of LEDs in slit lamp illumination.

In another embodiment, FIG. 2 shows an arrangement for homogenizing the light from the radiation sources on the basis of a hollow integrator.

The light coming from the sources of radiation 1 is collimated by a condenser lens 2 and imaged into the hollow integrator 4.

Due to reflections within the hollow integrator 4, the light from the sources of radiation 1 is homogenized and in the image plane 6 in which a slit diaphragm may be arranged, too, in order to generate the slit illumination required for a slit lamp. The slit thus generated is projected into the eye 9 via the projection device 7 and a deflecting prism 8, with the illumination's angle of incidence being variable.

The two aforementioned alternative embodiments for homogenization, which can be realized in a particularly compact and inexpensive manner, have similar properties in optical terms.

This ensures that the entire emitted radiation is transmitted to the ophthalmic examination device by the projecting unit. Due to the use of digital camera units, sources of radiation having a planar, rectangular emitting surface are optimal.

This advantageous embodiment results in improved efficiency and in the reduction of temperature-dependent effects.

Moreover, the considerably more homogeneous illuminated field improves the multiplicity of possible diagnoses and their reliability.

The time sequence, duration and intensity of the sources of radiation will be controlled and monitored individually or jointly or in groups by the control unit in order to generate special illumination spectra.

In this connection, the control of the one or more camera units can be tuned to the wavelengths of the light emitted by the illumination module and can be synchronized with their duration of light emission.

For example, at least one, but preferably more images can be recorded in the case of different-color states of illumination with an exposure time of several milliseconds. These monochromatic recordings can then be combined to form a color image. It is also possible to selectively evaluate differences in monochromatic recordings.

This embodiment has the advantage that no mechanically moved filters are required, that different diagnoses can be carried out using just one instrument, that temporal modulation of the source of radiation and synchronous, dedicated recording allow several monochromatic recordings to be realized, which are evaluated or combined to form a mixed chromatic image, without increasing the patient's exposure to radiation.

In addition, the optical power and/or the geometry of the light emitted by the sources of radiation is determined, monitored and configured in order to keep the eye's exposure to radiation as low as possible and within the allowed limits.

Thus, when changing the illumination patterns, this further results in the possibility of automatically adapting the radiation power and of re-adjusting type-dependent fluctuations in the properties of the source of radiation, in particular fluctuations in intensity which may also be caused by aging.

For compliance with the eye's allowed exposure to radiation, important settings of the ophthalmic instrument, such as currents and/or voltages, for example, should be monitored by the control unit in order to determine the dose of radiation. In doing so, a distinction should be made between wavelength-specific hazards, such as thermal and photochemical hazards for the eye.

In a case critical for safety, the control unit should comprise means for respectively reducing or switching off the supply of the source of radiation. The use of organic or inorganic sources of radiation with spectrally selective emission provides further considerable advantages.

On the one hand, such sources of radiation are characterized by a good dimming capacity at a nearly constant color temperature, with only an extremely slight shift (<0.02) of color loci in the chromaticity chart, causing a considerable improvement in the reproducibility of diagnostic results for different radiation powers of the source of radiation. Even warming of the sources of radiation leads to just a very slight shift of the color locus (of, for example, 0.0002/° C.) or of the peak wavelength (of, for example, 0.04 nm/° C.).

On the other hand, these sources of radiation are also characterized by very short switch-on and switch-off times (from 0% to 100% of the rated current), which are in the ms or even range. Thus, a particular working point (e.g. a specific current value) in the µs range can be switched on and switched off again by means of pulse width modulation, and brightness control can be effected with an identical working point. This results in a further possibility of stabilizing the color temperature and, thus, of improved reproduction of diagnostic results at different radiation powers of the source of radiation.

Moreover, an improved signal/noise ratio is achieved, while the dose of light can be kept to a minimum by only briefly increased exposure to radiation.

Further, the sources of radiation enable a brief overexposure without damage, in which case the level of overexposure depends on its duration. The duration of an overexposure with 3 times the rated current is in the ms range for LEDs.

Not least, the sources of radiation have a comparatively long service life of over 10,000 h, depending on the type of source. This allows the development of a design for the entire ophthalmic instrument which does not envisage changing the source of radiation during operation.

Although no mechanically moved filters are required, optical filters make it possible, in particular in the UV and IR ranges, to limit the emitted spectra in a defined manner by cut-off filters. The cut-off wavelengths of the optical filters are typically 380, 400 or 420 nm in the UV range and 700 nm in the IR range.

In order to guarantee sufficient light power, it should be ensured that the employed sources of radiation have a minimum optical power and that the light is emitted by the emitting surface in a spatially uniform manner. Further, the intensity of the source of radiation should be continuously adjustable over a wide range and the color temperature mostly constant over the entire intensity adjustment range.

Ophthalmic instruments common nowadays achieve powers of 10 to 20 W in the visible spectral region (400-700 nm), which corresponds to an optical power of approximately 1 W.

On the other hand, in the non-visible, infrared spectral range (700-1000 nm) as well as in the case of monochromatic sources of radiation, optical powers of only approximately 0.1 W are achieved.

In a particularly advantageous embodiment, the illumination device which consists of a source of illumination and of a projection device additionally comprises devices for geometric and/or spectral manipulation of the emitted light, which are selectively used.

In this case, the source of radiation serves to generate radiation, the manipulating device serves to generate geometric and/or spectral illumination patterns and the focusing optics serve to project the illumination patterns onto and/or into the eye.

This allows to generate special light patterns, such as slit illumination, or the like. However, it is also possible to optionally arrange optical filters, which may be selectively swiveled in and out, in the beam path, which filters preferably have wavelength-selective properties, such as high pass, low pass or bandpass filters, for example.

In order to avoid disturbing light influences during visual and/or digital observation, recording or output, it is common to geometrically split the illumination beam path and the observation beam path. A suitable technical solution consists in using a centrally arranged, vertical slit (slit prism) for illumination, and observation is preferably effected past the side thereof.

The control unit may be both integrated into the ophthalmic examination instrument or provided as a separate unit, connected via data links, and serves both to control the sources of radiation and the manipulating means in order to generate a continuous and/or pulsed, structured illumination, as well as to control the digital camera unit for visual and/or digital observation, recording or output of the images of the examined areas of the eye.

A separately provided control unit preferably comprises a user interface including an actuating unit, a keyboard, a display and a data output unit, in which case standard PC interfaces are preferably used as data links. Data output is preferably effected via printers or standardized interfaces. Of course, it is also possible to store the data on various data carriers, such as diskette, CD ROM, DVD, various memory cards, or the like.

Optionally, the device for generating and manipulating illumination patterns can be controlled electronically in order to facilitate communication with the control unit. The corresponding sources of radiation are controlled by the control unit via the switch-on time and duration as well as via current and voltage such that the desired spectral illumination pattern is generated.

In addition to these integrated sources of radiation, these may also be provided as separate units, in which case the radiation is guided, for example via light conducting fibers, to the ophthalmic instrument and is coupled into the illumination beam path of the latter. Such a design has the advantage, in addition to enabling a very compact construction of the ophthalmic instrument, of enabling a very individual adaptability of the illumination to the respective problem to be solved.

In a further advantageous embodiment, the digital camera unit is provided such that it can be used as a unit for visual observation, in which case the image of the examined eye is output on a display which is provided on the camera or separately. In this case, for enlarged observation, optional use may be made, for example, of a contact glass.

It has turned out to be particularly advantageous if, in addition to the visual output of the examined eye's image, the display also represents important control and adjustment data of the entire ophthalmic system.

In addition to visual observation of the images of the eye's examined areas represented on the display by the digital camera unit, the digital camera unit serves, in particular, to record and output these images. For this purpose, the digital camera unit is controlled synchronously with the sources of radiation used.

In a simple and inexpensive embodiment, the digital camera unit consists of a commercially available consumer camera, which preferably stores the recordings digitally on a transportable storage medium, such as a compact flash card, an SD card, a memory stick, or the like. The data transfer for further processing and/or archiving can be effected at a later time on a separate PC with special software.

The control unit itself, or a PC system connected via a data link, serves to store the images of the examined eye, preferably in the form of a patient-related database. The system should enable both export and import of patient-related data, using standardized formats (e.g. DICOM), as well as editing and extraction of functional features from the digital camera recordings in order to obtain relevant information for optimal diagnosis.

In connection with the editing of the camera recordings, it is convenient that the recordings can be evaluated in terms of quality and image errors present and that they can be corrected, if necessary, by software with respect to image sharpness, contrast, pixel errors, trimming, distortions, chromatic errors, local shifting, or the like.

In an additional embodiment, the ophthalmic examination instrument comprises a unit (e.g. a beam splitter) by which a part of the radiation that is preferably variable can be coupled out to an existing optoelectronic interface. Various applicators can be coupled to this standardized interface. Further, electronic control and monitoring of the attached applicator are present here.

For example, a flexible light conductor in the form of a stepped or gradient fiber can then be connected for transmission of the optical radiation in order to provide separate, additional illumination. The flexible light conductor is used, for example, for scleral illumination, so that the eye can be illuminated "from behind", and in particular to observe/document the cornea, the iris, the lens, the capsule or any implants present. The flexible light conductor(s) may also be used for regressive illumination.

Further, it is possible for a flexible light conductor to be connected to an illuminating module which is mounted on the physician's head.

The relatively high efficiency of the illuminating unit also allows temporally limited, mobile operation, in which case the supply of the sources of radiation is provided by accumulators.

The proposed technical solution provides further advantageous embodiments.

Thus, for example, an increase in image sharpness of the electronic recordings of the eye can be achieved using optical image stabilization, by arranging a mechanically movable, optical element in front of the electronic image sensor used as a visualizing unit, said optical element allowing to compensate for any movements of the eye—especially in the case of longer exposure times. The same effect can be achieved if the electronic image sensor itself is mechanically movable. Both of these solutions for optical image stabilization require the detection of eye movements relative to the electronic image sensor. The detection of eye movements can be effected here by means of a sensor, using a corresponding evaluation algorithm, in which case the image sensor of the visualizing unit can also be used.

However, an increase in the image sharpness of the electronic recordings can also be achieved by using shorter exposure times for image recording, combined with higher light intensities of the source of radiation and/or methods of subsequent electronic amplification or editing of the image data.

In a further embodiment, the electronic camera used as a visualizing unit comprises several sensors. In one embodiment, each monochromatic source of radiation of the illuminating system has a sensor assigned to it in the observation beam path. Said assignment may be effected in the observation beam path, for example, by means of dichroic filters or a beam splitter/filter combination. This enables recording of several monochromatic images at exactly the same time.

The same effect of recording several monochromatic images at exactly the same time can be achieved by using a direct image sensor from Foveon Inc., Santa Clara (USA), of the Foveon® X3™ type.

The recording of two monochromatic recordings with a very slight time difference of few milliseconds can be effected by the use of an electronic camera comprising interline sensors for temporary storage of a recording, in which case the light sources must be able to realize very short switch-on and switch-off times in sequence. Such recordings having only a very slight time difference between them are achieved by first actuating the first monochromatic light source and the electronic sensor effecting a dedicated recording. This recording is temporarily stored in the interline registers of the electronic camera. The electronic sensor effects the second monochromatic recording immediately upon switch-off of the first light source and switch-on of the second light source. Next, both recordings are digitized by the camera and transmitted to the PC.

Due to the combination of a beam splitter or a dichroic mirror, respectively, with two cameras including interline sensors, even four monochromatic recordings can be made with a very slight time difference in the range of few milliseconds by means of a source of radiation which can be sequentially actuated.

In a further special embodiment, illumination is effected in the form of very narrow gaps ranging from 10 μm to 1 mm, for which purpose a laser source having a very low étendue and, above all, very small divergence is used. This type of illumination is used in slit lamps which allow details to be examined in the anterior region of the eye. Numerous diseases can be recognized with adjustable magnification and special lateral illumination by the so-called light gap. In this case, a short impulse in the range of from several µs to few milliseconds is transmitted into the eye. This radiation, scattered by the media of the eye, is recorded by an electronic camera, and optional use can be made of an optical filter which is transparent only for the exciting wavelength of the laser.

It is also possible to use several lasers of different wavelengths sequentially in time or at the same time. In this case, recording of the different wavelengths is effected by means of electronic image sensors, temporally assigned to the sources of radiation, or one single recording is made with simultaneous illumination by several laser sources. The scattered light recordings can also be subjected here to subsequent processing by means of software. The special slit illumination described here has the advantages of a very good signal/noise ratio and of a very great depth of focus.

The ophthalmic examination instrument according to the invention, which comprises spatially structured illumination, allows to observe and/or document specific areas of an eye. In particular, the proposed illumination device provides spectrally selective spectra of high intensities in the near UV range of >400 nm. Since the ocular media have the greatest scattering power in this range, very good diagnoses are possible.

As the proposed solution allows to dispense with a mydriatic, there is very little irritation of the eye. Also, due to the possibility of a diagnosis in the IR range, there is no narrowing of the pupil during observation. The diagnostic possibilities are considerably improved and the patient's exposure to radiation is reduced.

Advantageously, the selection of desired wavelengths can be effected by actuating selected monochromatic sources of radiation, so that mechanically moved optical filters are no longer required and the construction of the instrument is simplified.

Compared to the existing solution, this has the advantage that precisely just the wavelength specifically needed for diagnosis is emitted by the source of radiation, which also minimizes the patient's exposure to radiation. Due to the multiplicity of different selectable wavelengths, several diagnoses using only one apparatus are possible.

The quick switching times of the LEDs enable a simple temporal modulation of the source of radiation and synchronization with the camera unit.

Compared with conventional sources of radiation, the LEDs used herein have a considerably more uniform field of illumination, better efficiency, reduced temperature-dependent effects, a stable color temperature, improved efficiency, reduced thermal load and improved reproducibility of diagnostic results at different radiation powers of the source of radiation.

All these advantages result in improved diagnostic possibilities due to an improved signal/noise ratio and in increased reliability of the diagnoses made.

The invention claimed is:

1. An ophthalmic instrument with homogeneous illumination for observation and/or documentation of an eye, comprising:
   an illumination device including
      a source of illumination,
      a homogenizing unit receiving light emitted by the source of illumination, and
      a projection device receiving light from the homogenizing unit,
      wherein the source of illumination includes one or more organic or inorganic sources of radiation having spectrally selective emission, which generate continuous and/or pulsed illumination of very high homogeneity;
   a control unit that controls the illumination device and enables recording or output of images of the eye, via a visualizing unit, the control unit being adapted for visual and/or digital observation; and
   wherein the homogenizing unit homogenizes light emitted by the one or more organic or inorganic sources of radiation with respect to the light's intensity, color and angular spectrum.

2. The ophthalmic instrument according to claim 1, wherein the illumination device, further comprises selectively usable devices for geometric and/or spectral manipulation of the emitted light.

3. The ophthalmic instrument according to claim 1, wherein the source of illumination comprises LEDs, SLDs, lasers or OLEDs used individually or in combination as sources of radiation with spectrally selective emission.

4. The ophthalmic instrument according to claim 1, wherein the illumination device comprises several sources of radiation with spectrally selective emission and with the same and/or different intensity distributions as a function of the wavelength, which are imaged onto a common aperture by dichroic mirrors.

5. The ophthalmic instrument according claim 1, wherein the source of illumination comprises multiple sources of radiation distributed in intensity such that an intensity distribution of the sources of radiation is broadband, narrowband or monochromatic or combinations thereof.

6. The ophthalmic instrument according to claim 1, wherein the source of radiation has a minimum optical power and the light is emitted by the emitting surface in a spatially uniform manner.

7. The ophthalmic instrument according claim 1, wherein the intensity of the source of radiation is continuously adjustable over a wide adjustment range and the color temperature is substantially constant over the entire adjustment range.

8. The ophthalmic instrument according to claim 1, wherein the illumination device emits a broadband spectrum and comprises one or more sources of radiation which emit a monochromatic spectrum of from about 400 to 490 nm and are coated with a luminescent dye for color conversion.

9. The ophthalmic instrument according to claim 8, wherein the broad spectrum emitted ranges from a frequency of about 400 to about 700 nm.

10. The ophthalmic instrument according to claim 1, wherein the illumination device emits a broadband spectrum in a spectral range from about 700 to about 1,100 nm and the illumination device comprises one or more sources of radiation having a half width of at least 20 nm, and further comprising a digital camera unit having sensitivity in the spectral range for visual and/or digital observation, recording or output.

11. The ophthalmic instrument according to claim 1, wherein the illumination device is adapted for excitation of fluorescence and comprises at least one narrowband source of radiation emitting a substantially monochromatic spectrum and having a maximum half width of 50 nm.

12. The ophthalmic instrument according to claim 11, wherein the at least one narrowband source of radiation exhibits a Gaussian profile with a central peak.

13. The ophthalmic instrument according to claim 1, wherein time sequence, duration and intensity of the sources of radiation are controlled and monitored by the control unit individually, jointly or in groups.

14. The ophthalmic instrument according to claim 1, wherein the homogenizing unit comprises a light integrator or light mixer arranged preceding the sources of radiation.

15. The ophthalmic instrument according to claim 1, wherein the homogenizing unit comprises a hollow integrator or a microlens array.

16. The ophthalmic instrument according to claim 1, wherein an optical power and/or a geometry of the light emitted by the sources of radiation is determined, monitored and corrected by the control unit so as to minimize radiation exposure of the eye and to maintain the radiation exposure of the eye within preselected limits.

17. The ophthalmic instrument according to claim 1, further comprising a digital camera unit and an output display that presents an image of the eye for viewing, the output display being provided on the camera or separately.

18. The ophthalmic instrument according to claim 1, wherein the control unit is integrated or provided as a separate unit connected via data links.

19. The ophthalmic instrument according to claim 18, wherein the data links comprise standard PC interfaces.

20. The ophthalmic instrument according to claim 1, wherein the control unit is separately provided and comprises a user interface including an actuating unit, a keyboard, a display and a data output unit.

21. The ophthalmic instrument according to claim 1, further comprising a display that, in addition to a visual output of the image of the eye, displays control and adjustment data of the entire system.

22. The ophthalmic instrument according to claim 1, wherein the control unit controls the sources of radiation including reducing or switching off the supply of the source of radiation.

23. The ophthalmic instrument according to claim 1, wherein a unit of the source of radiation having spectrally selective comprises a narrowband-emission semi-conductor light source and an optical filter unit to effect further spectral restriction of emission.

24. The ophthalmic instrument according to claim 1, wherein time sequence, duration and intensity of the sources of radiation are controlled and monitored by the control unit individually, jointly or in groups so as to ensure compliance with allowed radiation exposure of the eye.

25. The ophthalmic instrument according to claim 1, further comprising at least one digital camera unit or one observation tube with an eyepiece used as a visualizing unit.

26. The ophthalmic instrument according to claim 1, further comprising an optical image stabilizer to reduce blurring of the electronic images of the eye.

27. The ophthalmic instrument according to claim 1, wherein the control unit reduces exposure times, while simultaneously increasing the radiation power of the sources of radiation to avoid blurring of electronic recordings of the eye.

28. The ophthalmic instrument according to claim 1, further comprising an optical grating or a prism for collinear imaging of several laser sources serving as sources of radiation.

29. The ophthalmic instrument according to claim 1, further comprising several image sensors and corresponding dichroic filters or beam splitter/filter combinations to record several monochromatic images of the eye simultaneously.

30. The ophthalmic instrument according to claim 1, further comprising an image sensor of the Foveon® X3™ type for recording several monochromatic images of the eye simultaneously.

31. The ophthalmic instrument according to claim 1, further comprising an electronic camera unit having interline sensors for temporary storage of a recording, to record several monochromatic images with a very slight time difference between them.

32. The ophthalmic instrument according to claim 1, wherein the illumination device is provided as a separate unit and further comprising a light conductor for transmission of the radiation generated.

* * * * *

UNITED STATES PATENT AND TRADEMARK OFFICE
CERTIFICATE OF CORRECTION

| | | |
|---|---|---|
| PATENT NO. | : 7,871,164 B2 | |
| APPLICATION NO. | : 12/281134 | |
| DATED | : January 18, 2011 | |
| INVENTOR(S) | : Egon Luther et al. | |

It is certified that error appears in the above-identified patent and that said Letters Patent is hereby corrected as shown below:

Title Page, Item (30)
    Foreign Application Priority Data lists "10 2006 010 105", but the actual number is "10 2006 101 105.7".

Col. 1, line 59, "limits the etndue of the source of illumination", should read "limits the étendue of the source of illumination".

Col. 7, lines 60-61. "which are in the ms or even range", should read "which are in the ms or even µs range".

Col. 13, claim 23, lines 35-36, reads: The ophthalmic instrument ... wherein a unit of the source of radiation having spectrally selective comprises a narrowband-emission ...

but should read, The ophthalmic instrument ...wherein a unit of the source of radiation having spectrally selective <u>emission</u> comprises a narrowband-emission...

Signed and Sealed this
Twenty-eighth Day of June, 2011

David J. Kappos
*Director of the United States Patent and Trademark Office*